United States Patent
Niebauer et al.

(10) Patent No.: US 9,204,815 B2
(45) Date of Patent: Dec. 8, 2015

(54) FREQUENCY ANALYSIS TOOL FOR CARDIAC RESYNCHRONIZATION

(71) Applicant: THE CLEVELAND CLINIC FOUNDATION, Cleveland, OH (US)

(72) Inventors: Mark Niebauer, Mayfield Hts., OH (US); Cristian Pasluosta, Cleveland, OH (US); Niraj Varma, Cleveland Hts., OH (US)

(73) Assignee: The Cleveland Clinic Foundation, Cleveland, OH (US)

( * ) Notice: Subject to any disclaimer, the term of this patent is extended or adjusted under 35 U.S.C. 154(b) by 99 days.

(21) Appl. No.: 13/886,948

(22) Filed: May 3, 2013

(65) Prior Publication Data
US 2013/0296726 A1    Nov. 7, 2013

Related U.S. Application Data

(60) Provisional application No. 61/642,499, filed on May 4, 2012.

(51) Int. Cl.

| A61B 5/0452 | (2006.01) |
|---|---|
| A61B 5/04 | (2006.01) |
| A61B 5/042 | (2006.01) |
| A61B 5/0472 | (2006.01) |
| A61N 1/362 | (2006.01) |
| A61N 1/368 | (2006.01) |
| A61N 1/372 | (2006.01) |
| A61B 5/00 | (2006.01) |

(52) U.S. Cl.
CPC .............. *A61B 5/0452* (2013.01); *A61B 5/042* (2013.01); *A61B 5/04014* (2013.01); *A61B 5/0422* (2013.01); *A61B 5/0472* (2013.01); *A61N 1/3627* (2013.01); *A61N 1/3686* (2013.01); *A61N 1/37247* (2013.01); *A61B 5/726* (2013.01); *A61B 5/7257* (2013.01); *A61B 5/7264* (2013.01)

(58) Field of Classification Search
CPC ............ A61N 1/3627; A61N 1/37247; A61N 1/3686; A61B 5/0472; A61B 5/0452; A61B 5/0422; A61B 5/042; A61B 5/04014; A61B 5/7264; A61B 5/726
See application file for complete search history.

(56) References Cited

U.S. PATENT DOCUMENTS

| 7,440,804 | B1 * | 10/2008 | Min et al. | 607/28 |
|---|---|---|---|---|
| 2007/0232949 | A1 | 10/2007 | Saksena | |
| 2008/0021336 | A1 * | 1/2008 | Dobak | 600/508 |
| 2009/0281441 | A1 | 11/2009 | Zhang | |
| 2014/0222099 | A1 * | 8/2014 | Sweeney | 607/25 |

OTHER PUBLICATIONS

International Search Report and Written Opinion, mailed Jul. 3, 2013, pp. 1-14.

(Continued)

*Primary Examiner* — Michael Kahelin
(74) *Attorney, Agent, or Firm* — Tarolli, Sundheim, Covell & Tummino LLP

(57) ABSTRACT

Systems and methods are provided for evaluating an expected effectiveness of cardiac resynchronization therapy. Electrocardiogram (ECG) data is received as at least one ECG lead from a set of electrodes. A frequency spectrum representing the ECG data is generated via a Fourier transform. At least one predictor value is extracted from the calculated frequency spectrum. A fitness parameter, representing the expected effectiveness of cardiac resynchronization, is determined from at least the extracted predictor value.

10 Claims, 4 Drawing Sheets

(56) References Cited

OTHER PUBLICATIONS

Lecoq et al., Clinical and Electrocardiographic Predictors of a Positive Response..., The European Society of Cardiology, 2005, 26, 1094-1100.

Xia et al., "Predicting Effectiveness of Cardiac Resynchronization Therapy Based on QRS Decomposition Using the Meyer Orthogonal Wavelet Transformation", Heart Research Follow-up Program, Cardiology Unit, University of Rochester, Rochester NY, 4 pages.

* cited by examiner

FREQUENCY ANALYSIS TOOL FOR CARDIAC RESYNCHRONIZATION

RELATED APPLICATION

This application claims priority from U.S. Provisional Patent Application Ser. No. 61/642,499, filed 4 May 2012, the subject matter of which is incorporated hereby incorporated by reference in its entirety.

FIELD OF THE INVENTION

The present invention relates to systems and methods for regulating the function of a heart in a living being and, in particular, is directed to systems and methods for enhancing the application of cardiac resynchronization therapy.

BACKGROUND OF THE INVENTION

Congestive heart failure (CHF) now afflicts over 4 million Americans, and at least 400,000 new cases are found each year. The 5-year mortality of patients newly diagnosed with congestive heart failure is fifty percent, despite the best medical efforts. Most congestive heart failure cases are the result of impaired systolic function due to ischemic heart disease or idiopathic dilated cardiomyopathy. Impaired systolic function, in turn, can result in interventricular dyssynchrony. Interventricular dyssynchrony occurs when there is a delay between right ventricular (RV) and left ventricular (LV) activation. Interventricular dyssynchrony is particularly likely in the presence of left bundle branch block, in which RV contraction will precede LV contraction, leading to decreased LV ejection fraction.

Physiological benefits of CRT have included improved autonomic function, partial reversal of LV remodeling, improved LV function, and improved myocardial efficiency as well as decreased mitral regurgitation (MR). Echocardiographic strain-mapping studies have suggested that the improvement in MR may be due to restoration of synchronized papillary muscle function. Clinical trials have shown improved functional class, quality of life, and exercise tolerance. A meta-analysis of randomized, controlled trials that collectively evaluated a total of 1634 patients found that CRT was associated with a 51% reduction in death from progressive heart failure, a 29% reduction in heart failure hospitalization, and a trend toward a reduction of all-cause mortality. Despite these promising findings, CRT is still associated with limitations. A substantial proportion (25% to 30%) of patients who undergo CRT may not respond to therapy.

SUMMARY OF THE INVENTION

In accordance with an aspect of the present invention, a method is provided for evaluating ventricular pacing sites for cardiac resynchronization therapy (CRT). Ventricular pacing is applied at a first pacing site. Electrocardiogram (ECG) data representing the first pacing site is obtained from a set of electrodes as an ECG lead. A predictor value representing a frequency component of the ECG lead is extracted from the ECG data. A fitness parameter is determined for the first pacing site from at least the extracted predictor value. The fitness parameter is displayed to a user at an associated display.

In accordance with another aspect of the present invention, a non-transitorty computer readable medium stores machine executable instructions for evaluating an expected effectiveness of cardiac resynchronization therapy. Electrocardiogram (ECG) data is received as at least one ECG lead from a set of electrodes. A frequency spectrum representing the ECG data is generated via a Fourier transform. At least one predictor value is extracted from the calculated frequency spectrum. A fitness parameter, representing the expected effectiveness of cardiac resynchronization, is determined from at least the extracted predictor value.

In accordance with yet another aspect of the present invention, a system is provided for evaluating an expected effectiveness of cardiac resynchronization therapy. A signal processor is configured to receive a plurality of ECG leads and isolate a portion of interest from each of a proper subset of the ECG leads. A predictor extraction component is configured to extract respective predictor values representing frequency components of each of the isolated portions of interest. A parameter calculation component is configured to determine a parameter representing the likelihood that the patient will benefit from CRT from the extracted predictor values.

BRIEF DESCRIPTION OF THE DRAWINGS

The foregoing and other features of the present invention will become apparent to those skilled in the art to which the present invention relates upon reading the following description with reference to the accompanying drawings, in which.

DETAILED DESCRIPTION OF THE INVENTION

The practice of cardiac resynchronization therapy (CRT) is based on the observation that many patients with heart failure exhibit poorly coordinated contraction (dyssynchrony) of their ventricles compared to patients with normal cardiac function. This is often manifested by an abnormally wide QRS complex. A series of clinical studies have shown than CRT can significantly improve overall left ventricle contraction (shorten the QRS interval) and reduce heart failure symptoms in many patients undergoing this therapy. This therapy involves pacing the left ventricle at two sites to improve left ventricle function and is now used for heart failure patients with known markers of dyssynchrony. This invention is directed towards addressing the limitations of current CRT methodology which is compromised by a high rate of failures, referred to herein as non-responders. Specifically, current CRT offers no effective strategy to identify likely responders or convert non-responders to responders.

For example, selection of a left ventricular pacing site can be based on subjective criteria as well as anatomically available sites. When multiple sites on the left ventricle are available, implanters often choose sites that are often the easiest to access, since the effectiveness of a given site cannot be determined acutely, as the optimal left ventricle lead location can vary from patient to patient. Six months of observation may be necessary to determine whether a selected pacing site might be effective. The systems and methods described herein can be used during CRT device implantation as an objective aid to select the most effective pacing site of those available within the individual patient.

Figure 1:
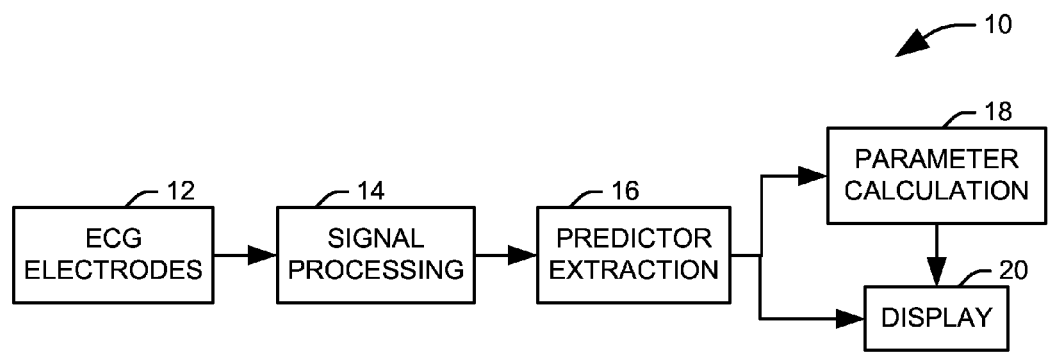
FIG. 1 an exemplary system for determining the effectiveness of cardiac resynchronization therapy (CRT) in accordance with an aspect of the present invention.

FIG. 1 illustrates an exemplary system 10 for determining the effectiveness of cardiac resynchronization therapy (CRT) in accordance with an aspect of the present invention. In the illustrated implementation, the system 10 is a stand-alone module that obtains electrocardiogram (ECG) signals through a set of ECG electrodes 12. It will be appreciated, however, that the system 10 could be implemented as machine executable instructions provided to an existing ECG apparatus, and utilize electrodes and signal processing components (e.g., filtering components, etc.) associated with that apparatus. Regardless of the specific implementation, the electrodes 12 can be arranged with any standard or specialized surface lead position. The ECG leads from the electrodes is provided to a signal processing component 14 to condition the signal and isolate any portions of the signal of interest for the analysis. In one implementation, the signal processing component 14 can isolate a QRS complex from each of a proper subset of the ECG leads, for example, from leads I, AVF, and V3. The signal processing component 14 can include one or both of analog and digital filtering components to remove noise from the ECG signals. The signal isolation process can be assisted by an operator or completely automated, depending on the implementation of the system.

A predictor extraction component 16 extracts a predictor value representing a frequency component of the ECG data from the processed data. For example, a frequency analysis of the ECG signal on one or more leads can be performed to provide a frequency domain representation of the signal, with the parameters drawn from the frequency domain representation. In one embodiment of the present invention, the frequency analysis is performed using a fast Fourier transform (FFT). In another embodiment of the present invention, the frequency analysis is performed using the Welch periodogram. In still another embodiment of the present invention, the frequency analysis is performed using autoregressive power spectrum (AR) analysis. In yet another embodiment, the frequency analysis is performed via a wavelet transformation of the ECG data. It will be appreciated that selected predictors can include maximum power within a frequency band of interest, a minimum power within the band, frequencies at the maximum and/or minimum power, a median frequency of the band (defined as the frequency for which half of the spectral power is at frequencies less than the frequency and half of the spectral power is at frequencies greater than the frequency), a total power under the curve of the within the band, intercepts (estimated or actual), rising or falling slope within the band, a mid-band fit, or any other appropriate parameters representing the frequency.

In one example, the predictor extraction component 16 can include dedicated hardware or machine readable instructions stored on a non-transitory computer readable medium for performing a continuous or discrete Fourier transform. The inventors have determined that patients who derive hemodynamic benefit from CRT are more likely to exhibit a shift in their QRS spectral content to higher frequencies than those who do not exhibit benefit from CRT. In addition, patients likely to benefit from CRT can exhibit higher frequencies in their QRS spectral content even in the baseline reading. Accordingly, the expected effectiveness of applied CRT can be evaluated from the spectral content of the QRS complex from a given patient. In this implementation, as applied to determination of a pacing site, the patient's baseline QRS frequency spectrum is first stored as a reference point in an associated memory, and the QRS power at various locations of the frequency spectrum can be identified. During the portion of the implant procedure when a left ventricular pacing site is chosen, candidate sites can be paced simultaneously with a standard right ventricular pacing site and the resulting QRS complexes recorded into the proposed device.

The extracted predictors are provided to a parameter calculation component 18 which determines a parameter representing the likelihood that the patient will benefit from CRT. The parameter calculation component 18 can comprise any appropriate expert system or group of expert systems configurable to determine the effectiveness of a proposed CRT for a patient. Examples of suitable systems can include artificial neural networks, support vector machines, Hidden Markov Models, rule based expert systems, and regression models. It will be appreciated that additional features unrelated to the frequency can be used for parameter calculation, including biometric parameters of the patient. It will be appreciated that data from the various leads can be used for extracting frequency spectra, such that features representing a given patient can be drawn from multiple frequency spectra representing multiple leads. In one implementation, information from different leads can be weighted differently. For example, the inventors have found information from lead V3 to be of particular value, and this increased value may be reflected in the operation of the parameter calculation component 18.

The change in the frequency spectrum at each site, along with an associated result from the parameter calculation component 18, can be displayed at an associated display 20. In one implementation, the frequency spectra associated with each of a plurality of pacing sites can be displayed in combination with the baseline spectrum to allow a user to compare the values to select an optimum site for the application of left ventricular pacing. Accordingly, the determination of the optimal site can be made by the operator from the display frequency spectra, completely automated, or made by operator guided by results from the parameter calculation component 18.

Figure 2:
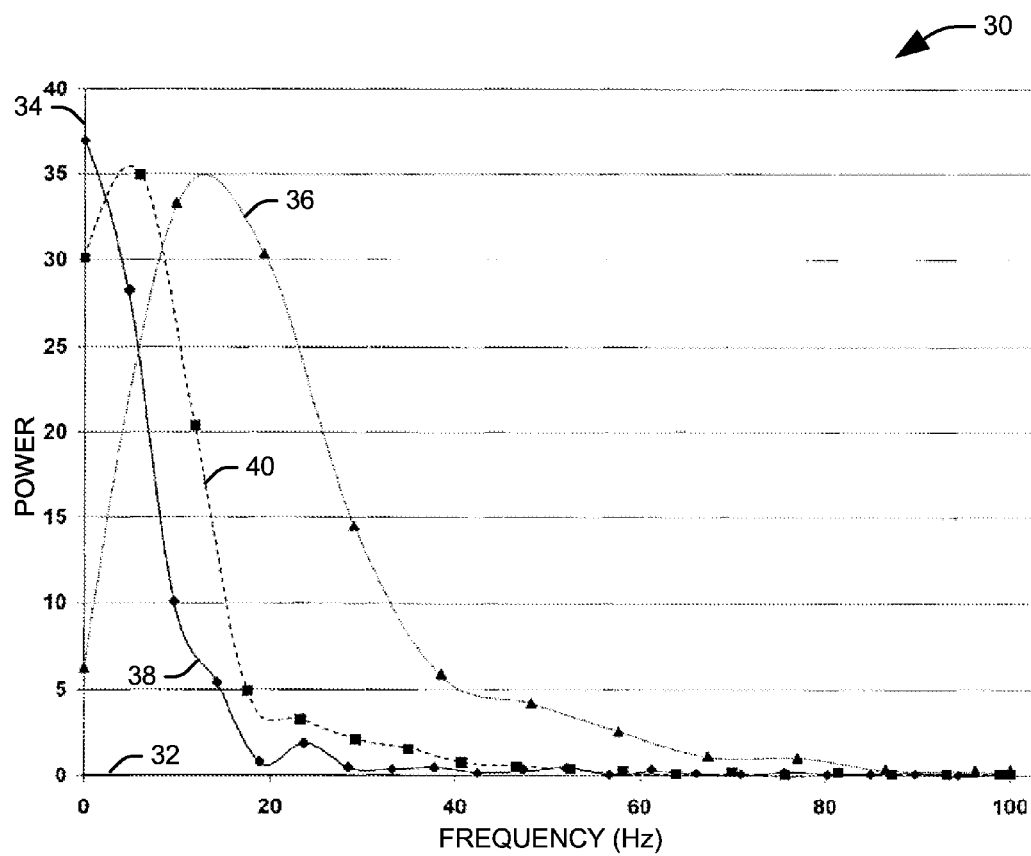
FIG. 2 is a chart illustrating exemplary frequency spectrums of the QRS complex.

FIG. 2 is a chart 30 illustrating exemplary frequency spectrums of the QRS complex, with the horizontal axis 32 representing signal frequency in hertz, and the vertical axis 34 representing the signal power at that frequency. For the purposes of the chart 30, it will be assumed that all of the frequency spectra 36, 38, and 40, represent QRS complexes isolated from a V3 lead, although it will be appreciated that signal data from other leads can be utilized. A dotted line 36 represents the frequency spectrum of the QRS complex for a first, healthy patient. It will be noted that the QRS complex of the healthy patient maintains significant power of a fairly broad range of frequencies. A solid line 38 represents the frequency spectrum of the QRS complex of a second patient who is experiencing a left branch bundle block. It will be noted that the frequency spectrum of the second patient is very narrow and drops off sharply as the frequency increases, such that a median frequency of that spectra is very low. A dashed line 40 represents the frequency spectrum of the second patient after CRT has been applied. It will be noted that the frequency spectrum has broadened significantly, increasing the median frequency of the signal. The inventors have determined that this broadening of the frequency spectrum to higher frequencies, quantified as the increase in median frequency, is an indicator that the CRT is likely to be successful with the left ventricle leads at the current pacing site.

Figure 3:
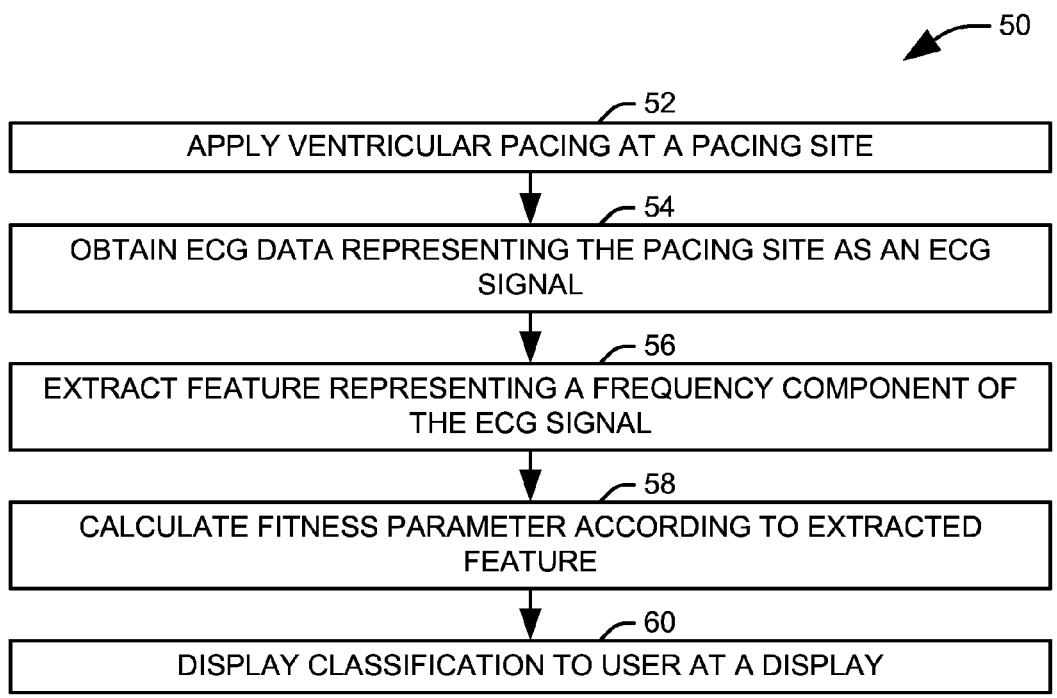
FIG. 3 illustrates a methodology for evaluating an optimal left ventricular pacing site for CRT in accordance with an aspect of the present invention
Figure 4:
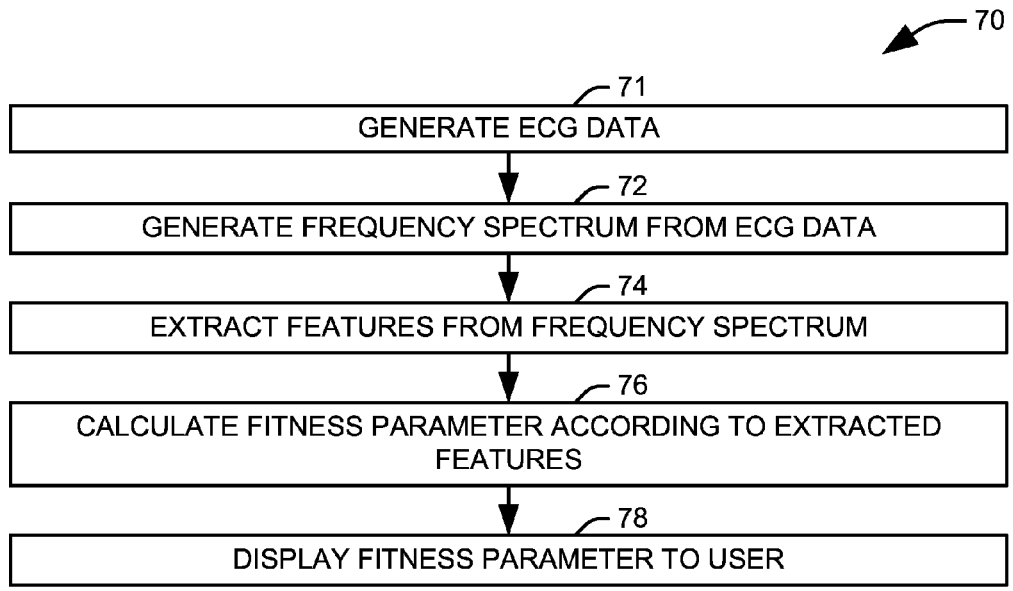
FIG. 4 illustrates a method for determining if a patient is a candidate for CRT in accordance with an aspect of the present invention.
Figure 5:
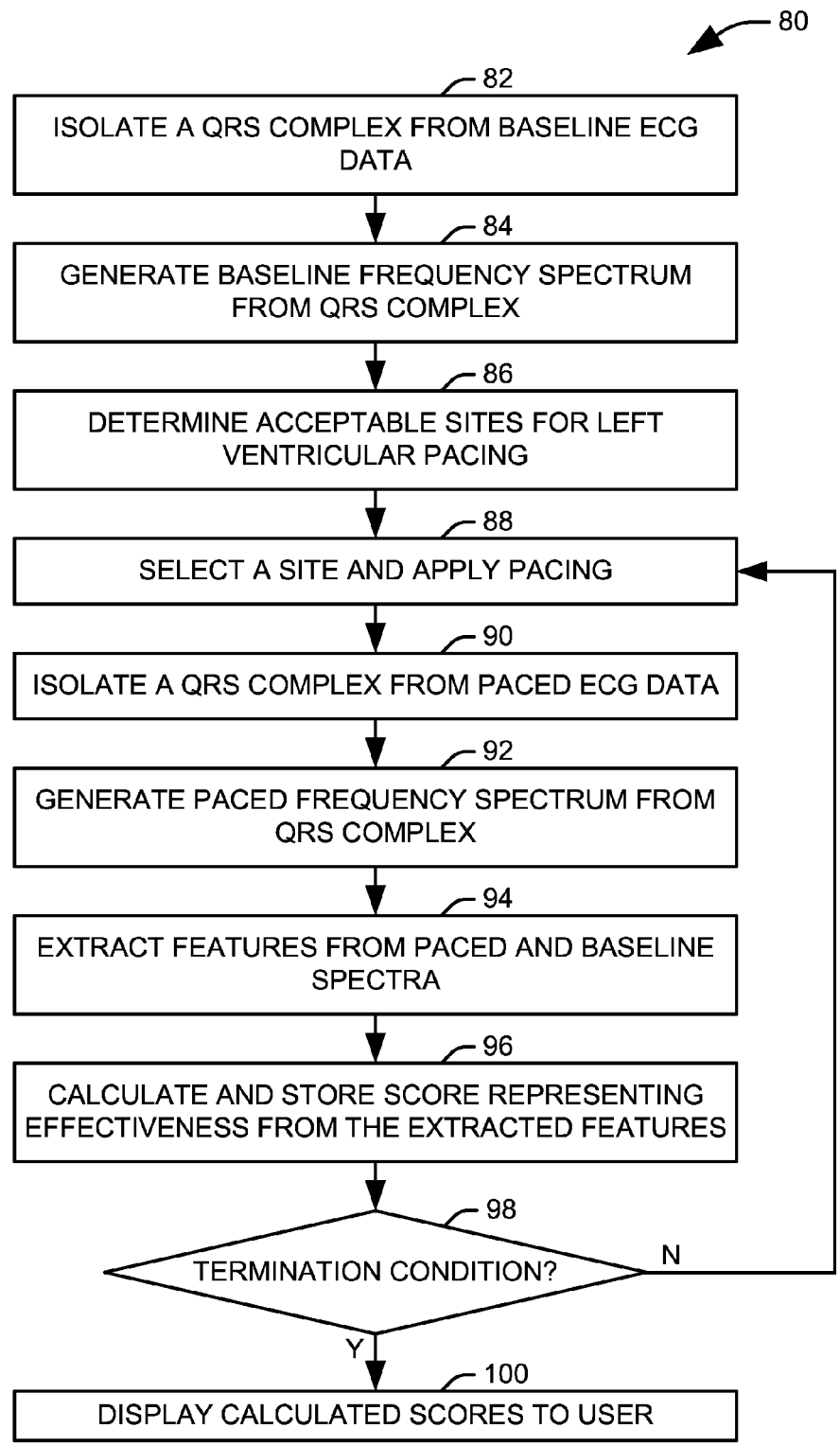
FIG. 5 illustrates a method for determining an optimal left ventricular pacing site for CRT in accordance with an aspect of the present invention.

In view of the foregoing structural and functional features described above, methods in accordance with various aspects of the present invention will be better appreciated with reference to FIGS. 3-5. While, for purposes of simplicity of explanation, the methods of FIGS. 3-5 are shown and described as executing serially, it is to be understood and appreciated that the present invention is not limited by the illustrated order, as some aspects could, in accordance with the present invention, occur in different orders and/or concurrently with other aspects from that shown and described herein. Moreover, not all illustrated features may be required to implement a method in accordance with an aspect of the present invention.

FIG. 3 illustrates a method 50 evaluating a pacing site for cardiac resynchronization therapy (CRT) in accordance with an aspect of the present invention. At 52, ventricular pacing is applied at a selected pacing site. At 54, ECG data is collected as at least one ECG signal representing the pacing site. All or a portion of the data from the various ECG leads can be utilized. In one implementation, the QRS complex from the V3 lead is isolated for analysis. It will be appreciated that baseline data can be collected prior to application of the pacing at 52 as well to facilitate the analysis.

At 56, one or more features are extracted representing frequency characteristics of the ECG data. For example, the one or more features can include the power at various frequencies in one or more frequency spectra, a median power for the spectrum, a total power represented by the frequency spectrum, or coefficients generated as part of a wavelet transform of the ECG data. In one implementation, one feature can include an increase in a power of the signal above ten hertz over a baseline value after application of the ventricular pacing. At 58, a fitness parameter is calculated for the patient from the extracted feature. For example, the extracted feature can be provided to a classification or regression model to provide a result representing the likelihood that pacing at the selected site will be successful. It will be appreciated that other features can be used in this determination, including age, sex, left ventricle end systolic volume, duration of the QRS complex, and left ventricle ejection fraction. At 60, the fitness parameter can be provided to a user at an associated display.

FIG. 4 illustrates a method 70 for determining if a patient is a candidate for cardiac resynchronization therapy (CRT) in accordance with an aspect of the present invention. At 71, at ECG data representing the patient is generated. It will be appreciated that this information can be taken from the patient before any ventricular pacing is started to establish a baseline reading. In one implementation, the QRS complex from the V3 lead is used, but it will be appreciated that information from different leads or multiple leads can be used. At 72, the ECG data is converted into the frequency domain to produce respective frequency spectra. For example, a fast Fourier transform can be utilized to generate the frequency spectra.

At 74, one or more features are extracted from the frequency spectra. For example, the one or more features can include the power at various frequencies in the various spectra, a median power for the spectrum, or a total power represented by the frequency spectrum. In one implementation, one feature can include a median frequency of a frequency spectrum derived from the QRS complex on the V3 lead. It will be appreciated that other features can be used in this determination, including age, sex, left ventricle end systolic volume, duration of QRS complex, and left ventricle ejection fraction. At 76, the patient is classified as a responder or non-responder, representing an expected effectiveness of CRT for that patient, according to the extracted features. For example, the features can be provided to a classifier, such as an artificial neural network, a statistical classifier, or a support vector machine, that provides a class and confidence for the classification. At 78, the classification can be provided to a user at an associated display.

FIG. 5 illustrates a method 80 for determining an optimal left ventricular pacing site for cardiac resynchronization therapy (CRT) in accordance with an aspect of the present invention. At 82, at least one QRS complex is isolated from baseline ECG data from the patient. At 84, each QRS complex is converted into the frequency domain to produce respective frequency spectra. For example, a fast Fourier transform can be utilized to generate the baseline frequency spectra. At 86, a plurality of acceptable sites for pacing the left ventricle are determined. For example, a number of anatomically available sites can be determined from imaging of the chest cavity. At 88, a site is selected and left ventricular pacing is applied simultaneously with standard right ventricular pacing.

At 90, at least one QRS complex is isolated from ECG data from the patient. In one implementation, the QRS complex from the V3 lead is used, but it will be appreciated that information from different leads or multiple leads can be used. At 92, each QRS complex is converted into the frequency domain to produce respective frequency spectra. At 94, one or more features are extracted from the frequency spectra associated with the selected pacing site and the baseline frequency spectra. For example, the one or more features can include the power at various frequencies in the various spectra, a median power for the spectrum, or a total power represented by the frequency spectrum. In one implementation, one feature can include a median frequency of a frequency spectrum derived from the QRS complex on the V3 lead.

At 96, a score representing the effectiveness of the selected pacing site is calculated from the extracted features and stored. For example, the features can be provided to an expert system, such as an artificial neural network, a statistical classifier, or a support vector machine, that provides a confidence value representing the likelihood that the CRT will be successful at the selected pacing site. In one implementation, the score can be calculated by a rule-based system from the change in one or more features between the baseline frequency spectrum and the frequency spectrum associated with the pacing site. At 98, it is determined a termination condition has been achieved. For example, the method can be terminated if no additional pacing sites remain for evaluation or if the calculated score exceeds a threshold value. If not (N), the method returns to 88 to select a new pacing site. If so (Y), the calculated scores can be provided to a user at an associated display at 100.

Figure 6:
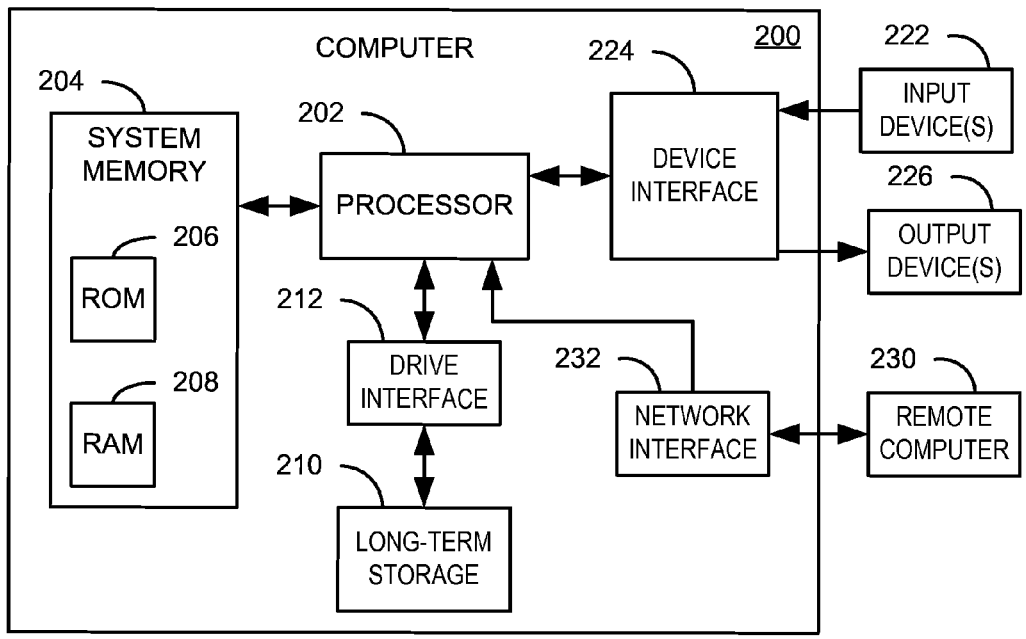
FIG. 6 illustrates a computer system that can be employed to implement systems and methods described herein.

FIG. 6 illustrates a computer system 200 that can be employed to implement systems and methods described herein, such as based on computer executable instructions running on the computer system. The user may be permitted to preoperatively simulate the planned surgical procedure using the computer system 200 as desired. The computer system 200 can be implemented on one or more general purpose networked computer systems, embedded computer systems, routers, switches, server devices, client devices, various intermediate devices/nodes and/or stand alone computer systems. Additionally, the computer system 200 can be implemented as part of the computer-aided engineering (CAE) tool running computer executable instructions to perform a method as described herein.

The computer system 200 includes a processor 202 and a system memory 204. Dual microprocessors and other multi-processor architectures can also be utilized as the processor 202. The processor 202 and system memory 204 can be coupled by any of several types of bus structures, including a memory bus or memory controller, a peripheral bus, and a local bus using any of a variety of bus architectures. The system memory 204 includes read only memory (ROM) 206 and random access memory (RAM) 208. A basic input/output system (BIOS) can reside in the ROM 206, generally containing the basic routines that help to transfer information between elements within the computer system 200, such as a reset or power-up.

The computer system 200 can include one or more types of long-term data storage 210, including a hard disk drive, a magnetic disk drive, (e.g., to read from or write to a removable disk), and an optical disk drive, (e.g., for reading a CD-ROM or DVD disk or to read from or write to other optical media). The long-term data storage 210 can be connected to the processor 202 by a drive interface 212. The long-term data storage 210 components provide nonvolatile storage of data, data structures, and computer-executable instructions for the computer system 200. A number of program modules may also be stored in one or more of the drives as well as in the RAM 208, including an operating system, one or more application programs, other program modules, and program data.

A user may enter commands and information into the computer system 200 through one or more input devices 222, such as a keyboard or a pointing device (e.g., a mouse). These and other input devices are often connected to the processor 202 through a device interface 224. For example, the input devices can be connected to the system bus by one or more a parallel port, a serial port or a universal serial bus (USB). One or more output device(s) 226, such as a visual display device or printer, can also be connected to the processor 202 via the device interface 224.

The computer system 200 may operate in a networked environment using logical connections (e.g., a local area network (LAN) or wide area network (WAN) to one or more remote computers 230. A given remote computer 230 may be a workstation, a computer system, a router, a peer device or other common network node, and typically includes many or all of the elements described relative to the computer system 200. The computer system 200 can communicate with the remote computers 230 via a network interface 232, such as a wired or wireless network interface card or modem. In a networked environment, application programs and program data depicted relative to the computer system 200, or portions thereof, may be stored in memory associated with the remote computers 230.

It will be understood that the above description of the present invention is susceptible to various modifications, changes and adaptations, and the same are intended to be comprehended within the meaning and range of equivalents of the appended claims. The presently disclosed embodiments are considered in all respects to be illustrative, and not restrictive. The scope of the invention is indicated by the appended claims, rather than the foregoing description, and all changes that come within the meaning and range of equivalence thereof are intended to be embraced therein.

Having described the invention, the following is claimed:

1. A method for evaluating ventricular pacing sites for cardiac resynchronization therapy (CRT) comprising:
    applying ventricular pacing at a first pacing site;
    obtaining electrocardiogram (ECG) data representing the first pacing site from a set of electrodes as an ECG lead;
    isolating a QRS complex from the ECG lead;
    extracting a predictor value representing a frequency component of a QRS complex within the ECG lead, the predictor value comprising one of a maximum power within a frequency band of interest, a minimum power within the frequency band of interest, frequencies having a maximum power, frequencies having a minimum power, a median frequency, a total power within the frequency band of interest, intercept values, a slope within the frequency band of interest, and a mid-band fit for the frequency band of interest;
    determining a fitness parameter for the first pacing site, representing the likelihood that the CRT will be successful at the first pacing site, from at least the extracted predictor value; and
    displaying the fitness parameter to a user at an associated display.

2. The method of claim 1, further comprising:
    obtaining baseline electrocardiogram (ECG) data from the set of electrodes; and
    extracting a baseline value representing a frequency component of the baseline ECG data;
    wherein determining the fitness parameter for the first pacing site from at least the extracted predictor value comprises calculating the fitness parameter for the first pacing site from at least the extracted predictor value and the extracted baseline value.

3. The method of claim 1, wherein extracting a predictor value representing the QRS complex within the frequency component of the ECG lead comprises performing a wavelet decomposition of at least a portion of the ECG lead.

4. The method of claim 1, wherein extracting a predictor value representing the QRS complex within the frequency component of the ECG lead comprises generating a Fourier transform of at least a portion of the ECG lead.

5. The method of claim 1, wherein determining a fitness parameter for the first pacing site from at least the extracted predictor value comprises providing the extracted predictor value to a classification model comprising at least one of a neural network, a support vector machine, and a hidden Markov model.

6. The method of claim 1, wherein obtaining electrocardiogram (ECG) data from the ECG lead comprises obtaining electrocardiogram (ECG) data from the V3 lead, and extracting the predictor value representing the frequency component of the ECG lead comprises extracting the predictor value as to represent a frequency component of the QRS complex within the V3 lead.

7. The method of claim 1, further comprising iteratively repeating the following steps until a termination condition is achieved:
    selecting a next pacing site from a plurality of available pacing sites;
    applying ventricular pacing at the selected pacing site;
    obtaining ECG data representing the selected pacing site from the ECG lead;
    extracting a predictor value representing a frequency component of the ECG data representing the selected pacing site; and
    determining a fitness parameter from at least the extracted predictor value representing the selected pacing site.

8. The method of claim 7, wherein the termination condition is the evaluation of all of the plurality of available pacing sites.

9. The method of claim 7, wherein the termination condition is the calculation of a fitness parameter above a threshold value.

10. The method of claim 1, wherein extracting a predictor value representing the QRS complex within the frequency component of the ECG lead comprises calculating a difference between a power of a baseline ECG signal, acquired prior to applying ventricular pacing, above ten hertz and a power of the ECG lead above ten hertz.

* * * * *